United States Patent
Tominaga

(10) Patent No.: US 8,323,629 B2
(45) Date of Patent: Dec. 4, 2012

(54) EXTERNAL PREPARATION FOR THE SKIN

(75) Inventor: Naoki Tominaga, Yokohama (JP)

(73) Assignee: Shiseido Company, Ltd., Chuo-ku, Tokyo (JP)

( * ) Notice: Subject to any disclaimer, the term of this patent is extended or adjusted under 35 U.S.C. 154(b) by 0 days.

(21) Appl. No.: 13/381,107

(22) PCT Filed: Jun. 23, 2010

(86) PCT No.: PCT/JP2010/004178
§ 371 (c)(1),
(2), (4) Date: Mar. 19, 2012

(87) PCT Pub. No.: WO2011/001633
PCT Pub. Date: Jan. 6, 2011

(65) Prior Publication Data
US 2012/0183492 A1 Jul. 19, 2012

(30) Foreign Application Priority Data
Jun. 29, 2009 (JP) ................. 2009-153988

(51) Int. Cl.
*A61K 8/02* (2006.01)
*A61K 31/74* (2006.01)

(52) U.S. Cl. .................. 424/78.03; 424/401; 514/112; 514/944

(58) Field of Classification Search .......... 424/401, 424/78.03; 514/112, 944
See application file for complete search history.

(56) References Cited

U.S. PATENT DOCUMENTS

| | | | |
|---|---|---|---|
| 5,422,112 A | 6/1995 | Williams | |
| 6,787,148 B1 | 9/2004 | Ueda et al. | |
| 2003/0198655 A1* | 10/2003 | Kaneda et al. | 424/401 |
| 2005/0175564 A1 | 8/2005 | Kaneda et al. | |
| 2008/0003246 A1* | 1/2008 | Smith et al. | 424/401 |

FOREIGN PATENT DOCUMENTS

| | | |
|---|---|---|
| JP | 05-139947 | 6/1993 |
| JP | 08-053322 | 2/1996 |
| JP | 10-218753 | 8/1998 |
| JP | 2002-284664 | 10/2002 |
| JP | 2004-043785 | 2/2004 |
| JP | 2005-068023 | 3/2005 |
| JP | 2005-343841 | 12/2005 |
| JP | 2006-062996 | 3/2006 |
| KR | 10-2009-0067019 | 6/2009 |
| WO | 01/17487 A1 | 3/2001 |
| WO | 03/095583 | 11/2003 |
| WO | 2005/117810 A1 | 12/2005 |
| WO | 2008/018541 A1 | 2/2008 |

OTHER PUBLICATIONS

Patent Abstract of Japan for Publication No. 05-139947, published Jun. 8, 1993, one page.
Patent Abstract of Japan for Publication No. 08-053322, published Feb. 27, 1996, one page.
Patent Abstract of Japan for Publication No. 10-218753, published Aug. 18, 1998, one page.
Patent Abstract of Japan for Publication No. 2002-284664, published Oct. 3, 2002, one page.
Patent Abstract of Japan for Publication No. 2005-068023, published Mar. 17, 2005, one page.
Patent Abstract of Japan for Publication No. 2006-062996, published Mar. 9, 2006, one page.
Espacenet Bibliographic Data, English Abstract of KR 10-2009-0067019, published Jun. 24, 2009, one page.
Espacenet Bibliographic Data, English Abstract of JP 2004-043785, published Feb. 12, 2004, one page.
Espacenet Bibliographic Data, English Abstract of JP 2005-343841, published Dec. 15, 2005, one page.
Korean Office Action and Partial English Translation dated Mar. 21, 2012, twelve pages.

* cited by examiner

*Primary Examiner* — Gina C Justice
(74) *Attorney, Agent, or Firm* — Rankin, Hill & Clark LLP

(57) ABSTRACT

An external preparation for skin has a pH value of 2.0-5.0 and comprises: (a) 1.0-7.0 mass % of at least one of the members selected from α-hydroxy acids, (b) 0.1-3.0 mass % of a crosslinked type N,N-dimethylacrylamide-2-acrylamido-2-methylpropanesulfonic acid sodium salt copolymer, and (c) 0.1-3.0 mass % of an associating thickener constituted of a compound of the formula (1): $R^1-\{(O-R^2)_k-OCONH-R^3[-NHCOO-(R^4-O)_n-R^5]_h\}_m$ (1) wherein $R^1$ represents a hydrocarbon group, $R^2$ and $R^4$ represent alkylene groups having 2-4 carbon atoms, which may be identical or different, or a phenylethylene group, $R^3$ represents a hydrocarbon group, which may have a urethane bond, $R^5$ represents a branched chain or secondary hydrocarbon group, m is a number of at least 2, h is a number of at least 1, k is a number within the range of 1-500, and n is a number within the range of 1-200.

17 Claims, No Drawings

EXTERNAL PREPARATION FOR THE SKIN

TECHNICAL FIELD

This invention relates to an external preparation for skin. This invention particularly relates to an external preparation for skin, which is excellent in usability and stability and which is adapted for use in improvement of skin, anti-aging of the skin, prevention and improvement of wrinkles, and the like. This invention also relates to a cosmetics kit containing the external preparation for skin.

BACKGROUND ART

Recently, as having the effects of peeling off an old stratum corneum in a skin surface, regenerating a new stratum corneum, and thus enhancing turnover (metabolism) of the epidermis, α-hydroxy acids, such as glycolic acid, lactic acid, malic acid, and tartaric acid, salicylic acid, trichloroacetic acid, phenol, and the like, have been contained in external preparations for skin, typically cosmetics. Also, the above-mentioned compounds are used for improvement of skin texture, a somber color on the skin, skin roughness, or the like, and for chemical peeling for the purposes of improvement of fine wrinkles, various types of pigmentation, such as spots, flecks, chloasmata, and senile pigment freckles, acne, dermatitis traces, fire burns, heat burns, traumata, and removal of wrinkles or spots on scar skins thereof. (Reference may be made to, for example, Patent Documents 1 and 2.) In order for the skin texture, the somber color on the skin, the acne, and the like, to be improved by use of the above-mentioned drugs, it is preferable that the drugs remain on the skin. However, the conventional external preparations for the chemical peeling have the problems in that the external preparations drip at the time of their use, and therefore their usability is bad. Also, in cases where large quantities of thickeners are contained in the external preparations for the thickening thereof, the problems are encountered in that the external preparations are difficult to wash away at the time of removal thereof.

As for techniques with which the thickeners are contained in the external preparations containing the α-hydroxy acids, and the like, there have heretofore been known, for example, attempts for increasing viscosities in compositions containing the α-hydroxy acids by the containing of a carboxyvinyl polymer and an α-hydroxy acid in a specific containing ratio, or by the containing of an α-hydroxy carboxylic acid, a heterobio-polysaccharide gum, such as a xanthan gum, an inorganic thickener, and a polyacrylamide in specific containing quantities. (Reference may be made to Patent Documents 3 and 4.) Further, in α-hydroxy acid containing external preparations which are currently available commercially, a xanthan gum or hydroxyethyl cellulose is used as the thickener.

However, the aforesaid conventional external preparations have bad viscosity stability and have the problems in that, though the external preparations have a high viscosity at the stage immediately after the production, the viscosity decreases markedly during storage, particularly during storage at high temperatures. Particularly, in cases the conventional external preparations contain the compounds, such as the α-hydroxy acids, in large containing quantities and have low pH values, it is not always possible for the external preparations to accomplish sufficient and stable thickening. Also, in cases where the quantities of the thickeners are increased, and the viscosities at the time of the production are set to be excessively high, the problems occur in that the usability of the external preparations becomes bad, or in that the external preparations are difficult to wash away at the time of removal from the skin.

PRIOR ART DOCUMENT

Patent Document

Patent Document 1: Japanese Unexamined Patent Publication No. 5 (1993)-139947
Patent Document 2: PCT Internal Publication No. WO 01/017487
Patent Document 3: Japanese Unexamined Patent Publication No. 10(1998)-218753
Patent Document 4: Japanese Unexamined Patent Publication No. 8(1996)-53322

SUMMARY OF THE INVENTION

Problems to be Solved by the Invention

In view of the above circumstances, the object of the present invention is to provide an external preparation for skin, which preparation contains an α-hydroxy acid and is adapted to be removed after being applied to skin, and which preparation has good viscosity stability at a low pH value, excellent usability, and excellent stability.

Means for Solving the Problems

The inventors eagerly conducted extensive research to solve the problems described above and have found that an external preparation for skin containing an α-hydroxy acids, which preparation is easy to wash away, while it has a moderate viscosity free from dripping, and which preparation is easy to apply to the skin, is obtained by the containing of specific thickeners in combination. The present has been made on the basis of the findings described above.

The present invention provides an external preparation for skin, comprising ingredients (a), (b), and (c), wherein the external preparation for skin has a pH value within the range of 2.0 to 5.0 and is adapted to be removed after being applied to the skin:

(a) at least one of the members selected from the group consisting of α-hydroxy acids, the ingredient (a) being contained in a containing quantity within the range of 1.0 to 7.0 mass %, (b) a crosslinked type N,N-dimethylacrylamide-2-acrylamido-2-methylpropane sulfonic acid sodium salt copolymer, the ingredient (b) being contained in a containing quantity within the range of 0.1 to 3.0 mass %, and (c) an associating thickener constituted of a compound that is represented by the following general formula (1), the ingredient (c) being contained in a containing quantity within the range of 0.1 to 3.0 mass %:

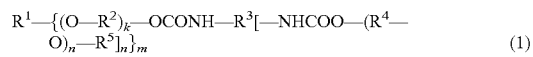

$$R^1-\{(O-R^2)_k-OCONH-R^3[-NHCOO-(R^4-O)_n-R^5]_n\}_m \quad (1)$$

wherein $R^1$ represents a hydrocarbon group, $R^2$ and $R^4$ independently represent alkylene groups having 2 to 4 carbon atoms, which alkylene groups may be identical or different from each other, or a phenylethylene group, $R^3$ represents a hydrocarbon group, which may optionally have a urethane bond, $R^5$ represents a branched chain or secondary hydrocarbon group, m represents a number of at least 2, h represents a number of at least 1, k represents a number within the range of 1 to 500, and n represents a number within the range of 1 to 200.

The present invention also provides a cosmetics kit, comprising the external preparation for skin in accordance with the present invention, a mask for use after the use of the external preparation for skin, and a night cream for use after the use of the mask.

Effects of the Invention

The external preparation for skin in accordance with the present invention, which preparation contains the α-hydroxy acid, is easy to wash away, while having a moderate viscosity free from dripping, and is easy to apply to the skin, is of low irritation, and is excellent in safety. Also, the external preparation for skin in accordance with the present invention has good viscosity stability and is excellent in effects of improvement of skin texture, a somber color on the skin, acne, and the like, which effects are inherent to chemical peeling.

Further, in cases where the external preparation for skin in accordance with the present invention further contains titanium oxide, a site to which the external preparation has been applied is capable of being confirmed visually after the application, and washing away residues are capable of being confirmed.

With the cosmetics kit in accordance with the present invention, which comprises the cosmetics to be used together with the external preparation for skin in accordance with the present invention, in cases where the user uses the cosmetics kit, the effects of the external preparation for skin in accordance with the present invention are obtained even further.

BEST MODE FOR CARRYING OUT THE INVENTION (a) At Least One of the Members Selected from the Group Consisting of α-Hydroxy Acids The α-hydroxy acid employed as the ingredient (a) in the external preparation for skin in accordance with the present invention has heretofore been used as a buffer or a neutralizer for cosmetics and cleaning preparations and has heretofore been contained in various kinds of cosmetics for the purposes of corneum softening, cell activation, and the like. The α-hydroxy acid contained in the external preparation for skin in accordance with the present invention is not limited particularly and may be, for example, glycolic acid, lactic acid, malic acid, tartaric acid, citric acid, glyceric acid, pyruvic acid, or mandelic acid. Among the above-enumerated α-hydroxy acids, glycolic acid, lactic acid, malic acid, or tartaric acid is preferable for its excellent effect of enhancing the turnover of the epidermis, and glycolic acid is more preferable. In the external preparation for skin in accordance with the present invention, each of the above-enumerated α-hydroxy acids may be contained alone or, if necessary, two or more of the above-enumerated α-hydroxy acids may be contained in combination.

The containing quantity of the aforesaid ingredient (a) in the external preparation for skin in accordance with the present invention is selected within the range of 1.0 to 7.0 mass % with respect to the total quantity of the external preparation for skin. The containing quantity of the aforesaid ingredient (a) should preferably be selected within the range of 2.0 to 6.0 mass %, and should more preferably be selected within the range of 3.0 to 5.0 mass %, with respect to the total quantity of the external preparation for skin. If the containing quantity of the ingredient (a) is smaller than 1.0 mass %, it will often occur that a sufficient effect of the chemical peeling is not obtained. If the containing quantity of the ingredient (a) is larger than 7.0 mass %, skin irritation will increase.

(b) Crosslinked Type N,N-Dimethylacrylamide-2-Acrylamido-2-Methylpropane Sulfonic Acid Sodium Salt Copolymer The crosslinked type N,N-dimethylacrylamide-2-acrylamido-2-methylpropane sulfonic acid sodium salt copolymer employed as the ingredient (b) in the external preparation for skin in accordance with the present invention should preferably be an N,N-dimethylacrylamide-2-acrylamido-2-methylpropane sulfonic acid sodium salt-N,N-methylenebisacrylamide copolymer, which is referred to also as a dimethylacrylamide/sodium acryloyl dimethyl taurate crosspolymer.

The dimethylacrylamide/sodium acryloyl dimethyl taurate crosspolymer may be produced by a method described in Japanese Patent No. 3708531.

The containing quantity of the aforesaid ingredient (b) in the external preparation for skin in accordance with the present invention is selected within the range of 0.1 to 3.0 mass % with respect to the total quantity of the external preparation for skin. The containing quantity of the aforesaid ingredient (b) should preferably be selected within the range of 0.5 to 2.0 mass %, and should more preferably be selected within the range of 1.0 to 1.5 mass %, with respect to the total quantity of the external preparation for skin. If the containing quantity of the ingredient (b) is markedly small, the problems will occur in that dripping is apt to occur due to a markedly low viscosity and in that, in cases where a desired viscosity is attained with the ingredient (c), the preparation becomes difficult to apply to the skin. If the containing quantity of the ingredient (b) is markedly large, the preparation will become difficult to wash away.

(c) Associating Thickener

The associating thickener employed as the ingredient (c) in the external preparation for skin in accordance with the present invention is the compound represented by the general formula (1) shown above.

The associating thickener is a copolymer having a hydrophilic group moiety as a skeleton and having hydrophobic moieties at terminals. Within a water-soluble medium, the hydrophobic moieties of the copolymer associate with each other, and the thickening effect is thereby obtained.

The hydrophobically modified polyurethane that is represented by the general formula (1) shown above is obtained by, for example, reacting at least one polyether polyol that is represented by the formula $R^1$—$[(O$—$R^2)_k$—$OH]_m$, at least one polyisocyanate that is represented by the formula $R^3$—$(NCO)_{h+1}$, and at least one polymonoalcohol that is represented by the formula HO—$(R^4$—$O)_n$—$R^5$.

In such cases, $R^1$ to $R^5$ in the general formula (1) are determined by the compounds $R^1$—$[(O$—$R^2)_k$—$OH]_m$, $R^3$—$(NCO)_{h+1}$ and HO—$(R^4$—$O)_n$—$R^5$. The loading ratios among the three compounds are not limited particularly and should preferably be such that the ratio of the isocyanate group derived from the polyisocyanate to the hydroxyl group derived from the polyether polyol and the polyether monoalcohol is selected within the range of NCO/OH of between 0.8:1 and 1.4:1.

The polyether polyol compound that is represented by the formula $R^1$—$[(O$—$R^2)_k$—$OH]_m$ and that may be used preferably for obtaining the associating thickener represented by the general formula (1) may be obtained from addition polymerization of an m-hydric polyol with an alkylene oxide, such as ethylene oxide, propylene oxide, butylene oxide, or epichlorohydrin, or with styrene oxide, and the like.

The polyols should preferably be di- to octa-hydric polyols. Examples of the di- to octa-hydric polyols include dihydric alcohols, such as ethylene glycol, propylene glycol, butylene glycol, hexamethylene glycol, and neopenthyl glycol; trihydric alcohols, such as glycerol, trioxy isobutane, 1,2,3-butanetriol, 1,2,3-pentanetriol, 2-methyl-1,2,3-propanetriol, 2-methyl-2,3,4-butanetriol, 2-ethyl-1,2,3-butanetriol, 2,3,4-pentanetriol, 2,3,4-hexanetriol, 4-propyl-3,4,5-heptanetriol, 2,4-dimethyl-2,3,4-pentanetriol, pentamethylglycerol, pentaglycerol, 1,2,4-butanetriol, 1,2,4-pentanetriol, trimethylolethane, and trimethylolpropane; tetrahydric alcohols, such as pentaerythritol, 1,2,3,4-pentanetetrol, 2,3,4,5-hexanetetrol, 1,2,4,5-pentanetetrol, and 1,3,4,5-hexanetetrol; pentahydric alcohols, such as adonitol, arabitol, and xylitol; hexahydric alcohols, such as dipentaerythritol, sorbitol, mannitol, and iditol; and octahydric alcohols, such as sucrose.

Also, $R^2$ is determined by the alkylene oxide, styrene oxide, or the like, which is subjected to the addition. Particularly, for availability and excellent effects, an alkylene oxide having 2 to 4 carbon atoms, or styrene oxide is preferable.

The alkylene oxide, styrene oxide, or the like, to be subjected to the addition may be subjected to single polymerization, or random polymerization or block polymerization of at least two members. The procedure for the addition may be the conventional procedure. Also, the polymerization degree k may be selected within the range of 0 to 1,000, preferably within the range of 1 to 500, and more preferably within the range of 10 to 200. Further, the ratio of the ethylene group occupying in $R^2$ should preferably be within the range of 50 to 100 mass % with respect to the total quantity of $R^2$. In such cases, the associating thickener appropriate for the purposes of the present invention is obtained.

Furthermore, the molecular weight of the polyether polyol compound that is represented by the formula $R^1—[(O—R^2)_k—OH]_m$ should preferably be selected within the range of 500 to 100,000, and should more preferably be selected within the range of 1,000 to 50,000.

The polyisocyanate that is represented by the formula $R^3—(NCO)_{n+1}$ and that may be used preferably for obtaining the hydrophobically modified polyether urethane represented by the general formula (1) employed in accordance with the present invention is not limited particularly in so far as the polyisocyanate has at least two isocyanate groups in the molecule. Examples of the polyisocyanates include aliphatic diisocyanates, aromatic diisocyanates, alicyclic diisocyanates, biphenyl diisocyanate, phenylmethane diisocyanate, phenylmethane triisocyanate, and phenylmethane tetraisocyanate.

Also, it is possible to employ dimmers and trimers (isocyanurate bonds) of the above-enumerated polyisocyanates. Further, it is possible to employ biuret obtained by a reaction with an amine.

Furthermore, it is possible to employ a polyisocyanate having a urethane bond obtained by a reaction of the aforesaid polyisocyanate compound and a polyol. As the polyol, di- to octa-hydric polyols are preferable, and the above-enumerated polyols are preferable. In cases where a tri- or higher-hydric polyisocyanate is used as the polyisocyanate that is represented by the formula $R^3—(NCO)_{n+1}$, it is preferable to employ the aforesaid polyisocyanate having the urethane bond.

The polyether monoalcohol that is represented by the formula $HO—(R^4—O)_n—R^5$ and that may be used preferably for obtaining the hydrophobically modified polyether urethane represented by the general formula (1) employed in accordance with the present invention is not limited particularly in so far as the polyether monoalcohol is a polyether of a straight chain, branched chain, or secondary monohydric alcohol. The polyether monoalcohol may be obtained by addition polymerization of the straight chain, branched chain, or secondary monohydric alcohol with an alkylene oxide, such as ethylene oxide, propylene oxide, butylene oxide, or epichlorohydrin, or with styrene oxide, and the like.

The compound represented by the general formula (1) may be produced by, for example, heating at a temperature of 80 to 90° C. for 1 to 3 hours and thereby causing a reaction to occur in the same manner as that in the ordinary reaction of a polyether and an isocyanate.

The associating thickener employed as the ingredient (c) in the external preparation for skin in accordance with the present invention should most preferably be a polyethylene glycol-240/decyltetradeceth-20/hexamethylene diisocyanate copolymer. The polyethylene glycol-240/decyltetradeceth-20/hexamethylene diisocyanate copolymer is referred to also as the polyethylene glycol-240/hexamethylene diisocyanate copolymer bis-decyltetradeceth-20 ether. The compound is commercially available as ADEKA NOL GT-700 (manufactured by ADEKA CO.).

The containing quantity of the aforesaid ingredient (c) in the external preparation for skin in accordance with the present invention is selected within the range of 0.1 to 3.0 mass % with respect to the total quantity of the external preparation for skin. The containing quantity of the aforesaid ingredient (c) should preferably be selected within the range of 0.5 to 2.0 mass %, and should more preferably be selected within the range of 1.0 to 1.5 mass %, with respect to the total quantity of the external preparation for skin. If the containing quantity of the ingredient (c) is markedly small, the problems will occur in that the dripping is apt to occur due to a markedly low viscosity and in that, in cases where a desired viscosity is attained with the ingredient (b), the preparation becomes difficult to wash away. If the containing quantity of the ingredient (c) is markedly large, the preparation will become difficult to apply to the skin.

The containing ratio (in mass ratio) of the ingredient (b) to the ingredient (c) should preferably be selected within the range of (b):(c) of between 1:0.6 and 1:1.5, and should more preferably be selected within the range of (b):(c) of between 1:0.6 and 1:1. If the containing ratio of the ingredient (c) with respect to the ingredient (b) is markedly low, the preparation will become difficult to wash away. If the containing ratio of the ingredient (c) with respect to the ingredient (b) is markedly high, the preparation will become difficult to apply to the skin.

(d) Titanium Oxide

In cases where the external preparation for skin in accordance with the present invention further contains the titanium oxide as the ingredient (d), by virtue of the coloring effect of the titanium oxide, the skin site to which the external preparation has been applied is capable of being confirmed visually after the application to the skin, and washing away residues are capable of being confirmed.

The external preparation for skin used in accordance with the present invention, which contains the α-hydroxy acid, should preferably be used for chemical peeling. For such purposes, after the external preparation for skin has been applied to the skin, the preparation is removed from the skin at the time at which a predetermined time has been elapsed. In such cases, ordinarily, if the base material used in the preparation is transparent, the washing away residues and wiping out residues will be difficult to perceive, and skin irritation will be caused to occur.

As the titanium oxide employed as the ingredient (d) in accordance with the present invention, ordinarily, the compounds used in the cosmetics field may be employed.

In cases where the ingredient (d) is contained, the containing quantity thereof in the total quantity of the external preparation for skin in accordance with the present invention may be selected within the range of 0.1 to 3.0 mass %, preferably within the range of 0.5 to 2.0 mass %, and more preferably within the range of 1.0 to 1.5 mass %. If the containing quantity of the ingredient (d) is smaller than 0.1 mass %, a sufficient coloring effect will not be obtained. Also, even if the containing quantity of the ingredient (d) is larger than 3.0 mass %, the coloring effect will not increase.

The external preparation for skin in accordance with the present invention has a pH value within the range of 2.0 to 5.0. From the view point of the skin irritation and the effects of the preparation, the pH value of the preparation should preferably be selected within the range of 3.0 to 5.0, and should more preferably be selected within the range of 3.5 to 4.5.

The external preparation for skin in accordance with the present invention should preferably have a viscosity selected within the range of 10,000 to 30,000 mPa·s/30° C., and should more preferably have a viscosity selected within the range of 20,000 to 25,000 mPa·s/30° C. In cases where the external preparation for skin in accordance with the present invention has the viscosity within the range described above, the preparation is obtained, which is optimum in usability, such as freedom from dripping, and ease of application to the skin.

No limitation is particularly imposed upon a neutralizer which may be contained in the external preparation for skin in accordance with the present invention. Examples of the neutralizers include potassium hydroxide, sodium hydroxide, sodium citrate, sodium carbonate, sodium hydrogencarbonate, ammonia, triethanolamine, L-arginine, and L-lysine. Particularly, sodium citrate and sodium hydroxide are preferable. In the external preparation for skin in accordance with the present invention, each of the above-enumerated neutralizers may be contained alone, or at least two of the above-enumerated neutralizers may be contained in combination.

The containing quantity of the neutralizer in the external preparation for skin in accordance with the present invention should preferably be selected within the range of 0.1 to 2.0 mass % with respect to the total quantity of the external preparation for skin, and should more preferably be selected within the range of 0.5 to 1.5 mass %.

No limitation is particularly imposed upon a technique for producing the external preparation for skin in accordance with the present invention. By way of example, the external preparation for skin in accordance with the present invention may be produced with a technique, wherein all ingredients are dissolved in purified water, wherein the resulting solution is subjected to a filtering process, and wherein a desired external preparation for skin is thereby obtained.

The external preparation for skin in accordance with the present invention is the external preparation of the type, in which the external preparation is applied to the skin, is left to stand for a predetermined period of time, and is thereafter removed from the skin. It is preferable that the external preparation for skin in accordance with the present invention is used as the external preparation for the chemical peeling. Ordinarily, as the way in which the external preparation for skin in accordance with the present invention is used as the external preparation for the chemical peeling, the way is taken in which the external preparation is applied to the skin, is left to stand for a predetermined period of time, and is thereafter washed away from the skin. It is also possible to wipe out the applied preparation by use of a wet cotton cloth or towel.

Particularly, in cases where the chemical peeling is to be performed by use of the external preparation for skin in accordance with the present invention, byway of example, the way of application described below may be taken.

Specifically, the operation comprising the steps of applying the external preparation for skin in accordance with the present invention to the skin, leaving the applied preparation to stand for a predetermined period of time, and thereafter washing away the applied preparation from the skin is repeated at intervals of 2 to 3 days, preferably at intervals of 2 days. In cases where the application of the external preparation for skin in accordance with the present invention to the skin is thus performed at the intervals of 2 to 3 days, particularly at the intervals of 2 days, the skin irritation accompanying continuous use which is performed otherwise is relieved, the effects of improving skin texture, a somber color on the skin, acne, and the like, are enhanced, and the skin beautifying effect enhanced even further is obtained. The period of time, during which the external preparation is left to stand after being applied to the skin, should preferably be selected within the range of approximately 3 to 5 minutes. The number of repetitions of the aforesaid operation may be at least one. Preferably, the aforesaid operation should be repeated at least 3 times, for example 3 to 7 times. In cases where the number of repetitions of the aforesaid operation is 3, the number of times of the application to the skin is 4 in total.

The term "external preparation for skin" as used herein is not limited particularly in so far as the external preparation is the preparation to be applied to the cortices. The term "external preparation for skin" as used herein embraces cosmetics, pharmaceuticals, quasi-drugs, and the like. Also, the external preparation for skin may be of any preparation form which has been thickened. Further, the external preparation for skin may take on the form supported on a sheet-shaped base material.

If necessary, besides the essential ingredients described above, the external preparation for skin in accordance with the present invention may also contain other arbitrary ingredients, which are ordinarily used in external preparations for skins, such as the cosmetics and the pharmaceuticals. Also, the external preparation for skin in accordance with the present invention may be produced by a conventional procedure in accordance with the desired preparation form. For example, the essential ingredients described above and at least one of the members selected from the ingredients described below may be contained together, and the external preparation for skin in accordance with the present invention may thereby be prepared.

Specifically, the external preparation for skin in accordance with the present invention may contain at least one ultraviolet light absorber. Examples of the ultraviolet light absorbers include benzoic acid types of ultraviolet light absorbers, such as para-aminobenzoic acid (hereinbelow abbreviated to PABA), a PABA monoglyceryl ester, an N,N-dipropoxy PABA ethyl ester, an N,N-diethoxy PABA ethyl ester, an N,N-dimethyl PABA ethyl ester, an N,N-dimethyl PABA butyl ester, and an N,N-dimethyl PABA methyl ester; anthranilic acid types of ultraviolet light absorbers, such as homomenthyl-N-acetyl anthranilate; salicylic acid types of ultraviolet light absorbers, such as amyl salicylate, menthyl salicylate, homomenthyl salicylate, octyl salicylate, phenyl salicylate, benzyl salicylate, and p-isopropanolphenyl salicylate; cinnamic acid types of ultraviolet light absorbers, such as octyl cinnamate, ethyl-4-isopropyl cinnamate, methyl-2,5-di-isopropyl cinnamate, ethyl-2,4-di-isopropyl cinnamate, methyl-2,4-di-isopropyl cinnamate, propyl-p-methoxy cinnamate, isopropyl-p-methoxy cinnamate, iso-amyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, glyceryl mono-2-ethylhexanoyl-diparamethoxy cinnamate, and a trimethoxycinnamic acid methylbis(trimethylsiloxane)silyl-isopentyl ester; 3-(4'-methylbenzylidene)-d,l-camphor; 3-benzylidene-d,l-camphor; urocanic acid; an urocanic acid ethyl ester; 2-phenyl-5-methylbenzoxazole; 2,2'-hydroxy-5-methylphenyl benzotriazole; 2-(2'-hydroxy-5'-t-octylphenyl)benzotriazole; 2-(2'-hydroxy-5'-methylphenyl)benzotriazole; dibenzalazine; di-anisoylmethane; 4-methoxy-4'-t-butyldibenzoylmethane; 5-(3,3-dimethyl-2-norbornylidene)-3-pentan-2-one; and dimorpholino pyridazinone.

Examples of ultraviolet light scattering agents, which may be used, include particles, such as titanium oxide employed as the ingredient (d), fine particle titanium oxide, zinc oxide, fine particle zinc oxide, iron oxide, fine particle iron oxide, and cerium oxide.

Ordinarily, the ultraviolet light scattering agents are used in the forms of acicular particles, spindle-shaped particles, spherical particles, and granular particles. Also, the ultraviolet light scattering agents should preferably be the fine particles having a particle diameter of at most 0.1 µm.

It is also preferable to use ultraviolet light scattering agents having been subjected to hydrophobising treatment, such as silicone treatment with a methyl hydrogen polysiloxane or a silane coupling agent; metallic soap treatment; fluorine treatment with a perfluoroalkylphosphoric acid diethanolamine salt, perfluoroalkylsilane, or the like; or dextrin fatty acid ester treatment.

Examples of liquid fats and oils, which may be used, include an avocado oil, a camellia oil, a turtle oil, a macadamia nut oil, a corn oil, a mink oil, an olive oil, a rapeseed oil, a yolk oil, a sesame oil, a persic oil, a wheat germ oil, a sasanqua oil, a castor oil, a linseed oil, a safflower oil, a cottonseed oil, a perilla oil, a soybean oil, a peanut oil, a tea seed oil, a kaya oil, a rice bran oil, a Chinese tung oil, a Japanese tung oil, jojoba oil, a germ oil, and triglycerol.

Examples of solid fats and oils, which may be used, include a cacao butter, a coconut oil, a horse tallow, a hydrogenated coconut oil, a palm oil, a beef tallow, a sheep tallow, a hydrogenated beef tallow, a palm kernel oil, a pig tallow, a beef bone tallow, a Japan wax kernel oil, a hydrogenated oil, a beef leg tallow, a Japan wax, and a hydrogenated castor oil.

Examples of waxes, which may be used, include a bees wax, a candelilla wax, a cotton wax, a carnauba wax, a bayberry wax, an insect wax, a whale wax, a montan wax, a rice bran wax, lanolin, a kapok wax, lanolin acetate, liquid lanolin, a sorgo wax, a lanolin fatty acid isopropyl ester, a lauric acid hexyl ester, a reduced lanolin, a jojoba wax, hard lanolin, a shellac wax, a POE lanolin alcohol ether, POE lanolin alcohol acetate, a POE cholesterol ether, a lanolin fatty acid polyethylene glycol, and a POE hydrogenated lanolin alcohol ether.

Examples of hydrocarbon oils, which may be used, include liquid paraffin, ozocerite, squalane, pristane, paraffin, ceresine, squalene, vaseline, a micro-crystalline wax, a polyethylene wax, and a Fischer-Tropsch wax.

Examples of higher fatty acids, which may be used, include lauric acid, myristic acid, palmitic acid, stearic acid, behenic acid, oleic acid, undecylenic acid, toluic acid, linoleic acid, linolenic acid, eicosapentaenoic acid (EPA), and docosahexaenoic acid (DHA).

Examples of higher alcohols, which may be used, include straight chain alcohols (such as lauryl alcohol, cetyl alcohol, stearyl alcohol, behenyl alcohol, myristyl alcohol, oleyl alcohol, and cetostearyl alcohol); and branched chain alcohols (such as a monostearyl glycerol ether (batyl alcohol), 2-decyl tetradecynol, lanolin alcohol, cholesterol, phytosterol, hexyl dodecanol, and octyl dodecanol).

Examples of synthetic ester oils, which may be used, include isopropyl myristate, cetyl octanoate, octyl dodecyl myristate, isopropyl palmitate, butyl stearate, hexyl laurate, myristyl myristate, decyl oleate, hexyl decyl dimethyl octanoate, cetyl lactate, myristyl lactate, lanolin acetate, isocetyl stearate, isocetyl isostearate, cholesteryl 12-hydroxy stearate, ethylene glycol di-2-ethyl hexanoate, a dipentaerythritol fatty acid ester, N-alkyl glycol mono-isostearate, neopentyl glycol dicaprate, di-isostearyl malate, glycerol di-2-heptyl undecanoate, trimethylolpropane tri-2-ethyl hexanoate, trimethylolpropane tri-isostearate, pentaerythritol tetra-2-ethyl hexanoate, glycerol tri-2-ethyl hexanoate, glycerol trioctanoate, glycerol tri-isopalmitate, trimethylolpropane tri-isostearate, cetyl-2-ethyl hexanoate, 2-ethyl hexyl palmitate, glycerol trimyristate, tri-2-heptylundecanoic acid glyceride, a castor oil fatty acid methyl ester, oleyl oleate, acetoglyceride, 2-heptyl undecyl palmitate, di-isobutyl adipate, an N-lauroyl-L-glutamic acid-2-octyl dodecyl ester, di-2-heptyl undecyl adipate, ethyl laurate, di-2-ethyl hexyl sebacate, 2-hexyl decyl myristate, 2-hexyl decyl palmitate, 2-hexyl decyl adipate, 2-ethyl hexyl succinate, tri-ethyl citrate, polyoxyethylene, and a polyoxypropylene random polymer methyl ether.

Examples of silicone oils, which may be used, include chain polysiloxanes (such as dimethyl polysiloxane, methyl phenyl polysiloxane, and diphenyl polysiloxane), cyclic polysiloxanes (such as octamethylcyclotetrasiloxane, decamethyl-cyclopentasiloxane, and dodecamethylcyclohexasiloxane), silicone resins in which three-dimensional network structures have been formed, silicone rubber, and various kinds of modified polysiloxanes (such as amino-modified polysiloxanes, polyether-modified polysiloxanes, alkyl-modified polysiloxanes, and fluorine-modified polysiloxanes).

Further, the external preparation for skin may contain lower alcohols, such as ethanol; anti-oxidants, such as butyl hydroxy toluene, tocopherol, and phytin; anti-microbial agents, such as benzoic acid, sorbic acid, a para-hydroxybenzoic acid alkyl ester, and hexachlorophene; organic acids, such as acyl sarcosine acid (e.g., sodium lauroyl sarcosine), and glutathione; vitamins, such as vitamin A and derivatives thereof, vitamin B, e.g., vitamin $B_6$ hydrochloride, vitamin $B_6$ tripalmitate, vitamin $B_6$ dioctanoate, vitamin $B_2$ and derivatives thereof, vitamin $B_{12}$, vitamin $B_{15}$ and derivatives thereof, vitamin C, e.g., ascorbic acid, an ascorbic acid sulfuric acid ester (salt), an ascorbic acid phosphoric acid ester (salt), and ascorbic acid dipalmitate, vitamin E, e.g., α-tocopherol, β-tocopherol, γ-tocopherol, and tocopherol acetate, vitamin D, vitamin H, pantothenic acid, and pantethine; various kinds of drugs, such as nicotinic acid amide, benzyl nicotinate, γ-oryzanol, allantoin, glycyrrhizinic acid (salt), glycyrrhetic acid and derivatives thereof, hinokitiol, bisabolol, thymol, inositol, saponins, e.g., saikosaponin, carrot saponin, loofah saponin, and mucrodisaponin, a pantothenyl ethyl ether, ethynyl estradiol, tranexamic acid, arbutin, cepharanthin, and a placenta extract; extracts of vegetables, such as *Rumex japonicus* Houtt., *Sophora flavescens* Aiton, *Nuphar japonicum* DC., orange, *Salvia officinalis* L., *Achillea alpina* L., *Malva sylvestris* L. var. *mauritiana* Mill. (Tree Mallow), Swertie Herb, *Thymus vulgaris* L. (Common Thyme), Japanese Angelica Root, Bitter Orange Peel, birch, *Equisetum arvense* L., loofah, *Aesculus hippocastanum* L (Horse Chestnut), *Saxifraga stolonifera* Meerb., *Arnica montana* L. (Arnica), lily, *Artemisia Princeps* Pampan., *Paeonia lactiflora* Pall., Aloe, *Gardenia jasminoides* Ellis forma *grandiflora* (Lour.) Makino, *Chamaecyparis pisifera* Endl., an extract of *Crataegus oxyacantha* L. (English Hawthorn), an extract of *Hypericum perforatum* L., an iris in extract, a Gambir extract, an extract of *Ginkgo biloba* L. (Ginkgo), an extract of *Thymus quinquecostatus* Celak., an extract of *Foeniculum vulgare* Mill. (Fennel), an oolong tea extract, a water lily extract, a Rose Fruit extract, an extract of *Isodon japonicus* (Burm.) Hara, a Scutellaria Root extract, a Phellodendron Bark extract, an extract of *Lamium album* L. var. *barbatum* (Sieb. et Zucc.) Franch. et Savat., a Glycyrrhiza Extract, an extract of *Gardenia jasminoides* Ellis forma *grandiflora* (Lour.) Makino, a black tea extract, a Chinese Tamarisk Twing extract, an extract of *Potentilla tormentilla* Schrank, a rose extract, a loofan extract, a peppermint extract, a rosemary extract, and a royal jelly extract; coloring matter; nonionic surfactants, such as sorbitan monolaurate, sorbitan monopalmitate, sorbitan sesquioleate, sorbitan trioleate, polyoxyethylene sorbitan monolaurate, polyoxyethylene sorbitan monostearate, polyethylene glycol monooleate, a polyoxyethylene alkyl ether, a polyglycol diether, lauroyl diethanol amide, fatty acid isopropanol amide, a maltitol hydroxy fatty acid ether, alkylated polysaccharides, alkyl glycosides, and a sugar ester; cationic surfactants, such as stearyl trimethyl ammonium chloride, benzalkonium chloride, and lauryl amine oxide; anionic surfactants, such as sodium palmitate, sodium laurate, sodium laurylate, potassium lauryl sulfate, an alkylsulfuric acid triethanol amine ether, a Turkey red oil, linear dodecylbenzene sulfate, polyoxyethylene hydrogenated castor oil maleate, and acyl methyl taurine; amphoteric surfactants; anti-oxidants, such as γ-tocopherol, and butyl hydroxy toluene; and antiseptics, such as phenoxy ethanol and paraben.

Besides the α-hydroxy acid, the external preparation for skin in accordance with the present invention may further contain the other arbitrary corneum peeling agent, such as N,N,N-trimethylglycine (TMG), L-serine, malonic acid, or succinic acid. In cases where the external preparation for skin in accordance with the present invention further contains the other arbitrary corneum peeling agent described above, the skin beautifying effect enhanced even further is obtained.

EXAMPLES

The present invention will further be illustrated by the following non-limitative examples. Unless otherwise specified, the containing quantity is expressed in terms of mass %.

Prior to the explanation of the examples, evaluation methods used in the present invention will be described hereinbelow. Also, a synthesis method for the ingredient (a) employed in the examples will be described hereinbelow.

(1) Effect Evaluating Method

By 20 special panelists, an actual usage test as described below was conducted by use of each of samples. Test items included the ease of pickup on a finger, the ease of application to the skin, the sliminess at the time of the washing away, and the ease of the washing away. With respect to each of the evaluation items, evaluation was made in accordance with the evaluation score criterion described below. Thereafter, the evaluation scores given by the respective panelists for each of the samples were summed up, and each of the samples was evaluated in accordance with the evaluation criterion described below.

(Actual Usage Test Method)

The external preparation for skin for use in the chemical peeling, which preparation had been prepared, was applied to the skin 4 times in total at intervals of 2 days by the special panelists with 10 panelists constituting one group. As the way of application, the external preparation for skin was picked up on a finger after face washing and was spread uniformly on the skin except for sites around the eyes, the site around the mouth, the naris, and the borders of the hair. The preparation having been applied was left to stand for 5 minutes and was then washed away sufficiently with running water or running tepid water for approximately 1 minute so as not to rub strongly.

The evaluation of the state free from irritation during the period during which the external preparation was applied to the skin, and the valuation of the skin state (a smooth feeling and a slippery feeling) were made in accordance with the evaluation score criterion described below. Thereafter, the evaluation scores given by the respective panelists for each of the samples were summed up, and each of the samples was evaluated in accordance with the evaluation criterion described below.

(Evaluation Score Criterion)
Score of 5: Markedly excellent.
Score of 4: Excellent.
Score of 3: Fair.
Score of 2: Poor.
Score of 1: Markedly poor.

(Evaluation Criterion)
Excellent (Exc.): The average score was within the range of 4, inclusive, to 5, inclusive.
Good: The average score was within the range of 3, inclusive, to less than 4.
Fair: The average score was within the range of 2, inclusive, to less than 3.
Poor: The average score was within the range of 1, inclusive, to less than 2.

(2) Synthesis of Crosslinked Type N,N-Dimethylacrylamide-2-Acrylamido-2-Methylpropane Sulfonic Acid Sodium Salt Copolymer Firstly, 35 g of dimethylacrylamide (manufactured by Kojin Co., Ltd.), 17.5 g of 2-acrylamido-2-methylpropanesulfonic acid (manufactured by Sigma), and 7 mg of methylenebisacrylamide were dissolved in ion-exchanged water, and the pH value of the resulting solution was adjusted at 7.0 by the addition of sodium hydroxide. Thereafter, 260 g of n-hexane, 8.7 g of polyoxyethylene (3) oleyl ether (EMULEX 503, manufactured by Nihon Emulsion Co., Ltd.), and 17.6 g of polyoxyethylene (6) oleyl ether (EMULEX 506, manufactured by Nihon Emulsion Co., Ltd.) were introduced into a 1,000 ml three-neck flask provided with a reflux device, were mixed together, and were thus subjected to dissolution. The inside atmosphere of the three-neck flask was then replaced by an $N_2$ gas. The aqueous monomer solution having been prepared in the manner described above was then introduced into the three-neck flask. The resulting mixture was heated to a temperature of 65° C. to 70° C. in an oil bath, while the mixture was being stirred under the $N_2$ gas atmosphere. At the stage at which the system had reached the temperature of 65° C. to 70° C., it was confirmed that the system had come into a semitransparent microemulsion state, and 2 g of ammonium persulfate was then added to the polymerization system. Polymerization was thus begun. The polymerization system was kept at the temperature of 65° C. to 70° C. with stirring, and a microgel was thus formed. After the polymerization had finished, acetone was added to the microgel suspension, and the microgel was thus precipitated. Subsequently, washing with acetone was performed three times, and the residual monomers and the surfactants were thus removed. The obtained precipitate was collected by filtration and dried under reduced pressure, and a white powder-like microgel dry product was thereby obtained.

Examples 1 to 10

Comparative Examples 1 to 3

External preparations for skin for use in chemical peeling, which were constituted of formulation ingredients listed in Table 1 and Table 2 shown below, were prepared by the processes (1) to (3) described below. With respect to the external preparations for skin for use in chemical peeling, which had been prepared, the ease of pickup on a finger, the ease of application to the skin, the sliminess at the time of the washing away, and the ease of the washing away were evaluated in accordance with the criteria described above. The results are shown in Table 1 and Table 2.

(1) Processes for Producing External Preparations of Examples 1 to 10

The crosslinked type N,N-dimethylacrylamide-2-acrylamido-2-methylpropane sulfonic acid sodium salt copolymer was dissolved in ion-exchanged water. Thereafter, glycolic acid was added to the resulting solution and dissolved therein, and the solution was neutralized by the addition of sodium hydroxide. The PEG-240/decyltetradeceth-20/HDI copolymer having been previously dissolved with heating in a part of purified water was mixed with the aforesaid solution. Thereafter, the remaining ingredients were dissolved, and the external preparation was obtained by filtration.

(2) Processes for Producing External Preparations of Comparative Examples 2 and 3

The crosslinked type N,N-dimethylacrylamide-2-acrylamido-2-methylpropane sulfonic acid sodium salt copolymer was dissolved in purified water. Thereafter, the remaining ingredients were dissolved, and the external preparation was obtained by filtration.

(3) Process for Producing External Preparation of Comparative Example 1

Glycolic acid was added to purified water and dissolved therein, and the resulting solution was neutralized by the addition of sodium hydroxide. The PEG-240/decyltetradeceth-20/HDI copolymer having been previously dissolved with heating in a part of purified water was mixed with the aforesaid solution. Thereafter, the remaining ingredients were dissolved, and the external preparation was obtained by filtration.

TABLE 1

| Contained ingredient | Ex. 1 | Ex. 2 | Ex. 3 | Ex. 4 | Ex. 5 | Comp. Ex. 1 | Comp. Ex. 2 | Comp. Ex. 3 |
|---|---|---|---|---|---|---|---|---|
| Purified water | 79.49 | 79.49 | 78.99 | 78.99 | 78.19 | 79.99 | 78.49 | 79.49 |
| Glycolic acid | 4 | 4 | 4 | 4 | 4 | 4 | 4 | 4 |
| Crosslinked type N,N-dimethylacrylamide-2-acrylamido-2-methylpropane sulfonic acid sodium salt copolymer | 0.5 | 1 | 1 | 1.5 | 2 | — | 3 | 1 |
| PEG-240/decyltetradeceth-20/HDI copolymer (*1) | 1.5 | 1 | 1.5 | 1 | 1.3 | 1.5 | — | — |
| Xanthan gum | — | — | — | — | — | — | — | 1 |
| Dynamite glycerol | 5 | 5 | 5 | 5 | 5 | 5 | 5 | 5 |
| 1,3-Butylene glycol | 5 | 5 | 5 | 5 | 5 | 5 | 5 | 5 |
| Sodium citrate | 1 | 1 | 1 | 1 | 1 | 1 | 1 | 1 |
| Sodium hydroxide | 1.2 | 1.2 | 1.2 | 1.2 | 1.2 | 1.2 | 1.2 | 1.2 |
| PPG-13 decyltetradeceth-24 | 0.5 | 0.5 | 0.5 | 0.5 | 0.5 | 0.5 | 0.5 | 0.5 |
| Phenoxy ethanol | 0.3 | 0.3 | 0.3 | 0.3 | 0.3 | 0.3 | 0.3 | 0.3 |
| Titanium oxide | 1.5 | 1.5 | 1.5 | 1.5 | 1.5 | 1.5 | 1.5 | 1.5 |
| Perfume | 0.01 | 0.01 | 0.01 | 0.01 | 0.01 | 0.01 | 0.01 | 0.01 |
| pH Value | 4 | 4 | 4 | 4 | 4 | 4 | 4 | 4 |
| Viscosity (mPa · s/30° C.) | 21,000 | 12,000 | 22,000 | 22,000 | 53,000 | 28,000 | 22,000 | 10,000 |
| Ease of pickup on a finger | Good | Exc. | Exc. | Exc. | Exc. | Poor | Exc. | Exc. |
| Ease of application to the skin | Good | Exc. | Exc. | Exc. | Exc. | Poor | Exc. | Exc. |
| Sliminess at the time of washing away | Exc. | Exc. | Exc. | Exc. | Good | Exc. | Poor | Poor |
| Ease of washing away | Exc. | Exc. | Exc. | Exc. | Good | Exc. | Poor | Poor |

TABLE 2

| Contained ingredient | Ex. 6 | Ex. 7 | Ex. 8 | Ex. 9 | Ex. 10 |
|---|---|---|---|---|---|
| Purified water | 79.49 | 75.99 | 81.99 | 81.09 | 77.89 |
| Glycolic acid | 4 | 7 | 1 | 4 | 4 |
| Crosslinked type N,N-dimethylacrylamide-2-acrylamido-2-methylpropane sulfonic acid sodium salt copolymer | 1.5 | 1.5 | 1.5 | 1.5 | 1.5 |
| PEG-240/decyltetradeceth-20/HDI copolymer (*1) | 0.5 | 1 | 1 | 1 | 1 |
| Xanthan gum | — | — | — | — | — |
| Dynamite glycerol | 5 | 5 | 5 | 5 | 5 |
| 1,3-Butylene glycol | 5 | 5 | 5 | 5 | 5 |
| Sodium citrate | 1 | 1 | 1 | 0.1 | 1 |
| Sodium hydroxide | 1.2 | 1.2 | 1.2 | — | 2.3 |
| PPG-13 decyltetradeceth-24 | 0.5 | 0.5 | 0.5 | 0.5 | 0.5 |
| Phenoxy ethanol | 0.3 | 0.3 | 0.3 | 0.3 | 0.3 |
| Titanium oxide | 1.5 | 1.5 | 1.5 | 1.5 | 1.5 |
| Perfume | 0.01 | 0.01 | 0.01 | 0.01 | 0.01 |

TABLE 2-continued

| Contained ingredient | Ex. 6 | Ex. 7 | Ex. 8 | Ex. 9 | Ex. 10 |
|---|---|---|---|---|---|
| pH Value | 4 | 4 | 4 | 2 | 5 |
| Viscosity (mPa · s/30° C.) | 13,000 | 20,000 | 30,000 | 14,000 | 11,000 |
| Ease of pickup on a finger | Exc. | Exc. | Exc. | Exc. | Exc. |
| Ease of application to the skin | Exc. | Exc. | Exc. | Exc. | Exc. |
| Sliminess at the time of washing away | Good | Exc. | Exc. | Exc. | Exc. |
| Ease of washing away | Good | Exc. | Exc. | Exc. | Exc. |

(*1)ADEKA NOL GT-700 (manufactured by ADEKA CO.)

With each of the external preparations for skin in accordance with the present invention (prepared in Examples 1 to 10), comprising glycolic acid, the crosslinked type N,N-dimethylacrylamide-2-acrylamido-2-methylpropane sulfonic acid sodium salt copolymer, and the PEG-240/decyltetradeceth-20/HDI copolymer, the ease of pickup on a finger was good or excellent, and the ease of washing away was markedly excellent.

With the external preparations for skin (prepared in Comparative Examples 2 and 3), comprising glycolic acid and the crosslinked type N,N-dimethylacrylamide-2-acrylamido-2-methylpropane sulfonic acid sodium salt copolymer alone, though the ease of pickup on a finger was acceptable, the ease of washing away was markedly poor. Also, with the external preparation for skin (prepared in Comparative Example 1), comprising glycolic acid and the PEG-240/decyltetradeceth-20/HDI copolymer alone, though the ease of washing away was acceptable, the ease of pickup on a finger was markedly poor.

Example 11

Cosmetics Kit

A cosmetics kit, comprising a day cream, a night cream, an essence (moisturizer), a mask, and the external preparation for skin having been prepared in Example 4 in accordance with the present invention, was prepared. As the day cream, the night cream, and the essence, the creams and the essence used ordinarily and available commercially were employed.

With the cosmetics kit, the essence and the day cream were used for morning care (morning operation 1). Also, the essence and the night cream were used for night care (night operation 1). Alternatively, the external preparation for skin having been prepared in Example 4, the mask, and the night cream were used for the night care (night operation 2).

As the way of use, for both the morning care and the night care, the cosmetics kit was used after the face washing. As the morning care, the morning operation 1 was performed every day. As the night care, the night operation 2 was performed at intervals of 2 days, for example, in the sequence of the night operation 2—the night operation 1—the night operation 1—the night operation 2—the night operation 1—the night operation 1—the night operation 2— . . . . Thus the night care was performed such that the night operation 2 might be carried out approximately 4 times. The night operation 2 was performed in the manner described below.

(1) The external preparation for skin having been prepared in Example 4 (Example 4 formulation) was picked up on a finger tip and was spread uniformly on the skin except for sites around the eyes, the site around the mouth, the naris, and the borders of the hair.
(2) The preparation having been applied was left to stand for 5 minutes and was then washed away sufficiently with running water or running tepid water for approximately 1 minute so as not to rub strongly.
(3) Thereafter, the mask having been sufficiently impregnated with the essence was put in close contact with the skin, and the beauty liquid ingredients were thus supplied to all areas of the face.
(4) The mask was removed from the skin at the time at which a period of time of approximately 10 minutes had elapsed, and the night cream was then applied to the skin.

Examples of formulations of the external preparations for skin in accordance with the present invention will be described hereinbelow. The present invention is not limited by the examples of the formulations described below and is specified by the claim described later. In the examples of the formulations described below, the containing quantity is expressed in terms of mass % with respect to the total quantity of the product.

Formulation Example 1

| (1) | Lactic acid | 3.0 mass % |
|---|---|---|
| (2) | Dipropylene glycol | 5.0 |
| (3) | Dynamite glycerol | 1.0 |
| (4) | Crosslinked type N,N-dimethylacrylamide-2-acrylamido-2-methylpropane sulfonic acid sodium salt copolymer | 1.3 |
| (5) | PEG-240/decyltetradeceth-20/HDI copolymer | 1.0 |
| (6) | Potassium hydroxide | 1.0 |
| (7) | Sodium citrate | 3.0 |
| (8) | Dipotassium glycyrrhizate | 0.05 |
| (9) | EDTA-2Na | 0.02 |
| (10) | Ethanol | 3.0 |
| (11) | PEG-60 hydrogenated castor oil | 0.3 |
| (12) | Phenoxy ethanol | 0.3 |
| (13) | Perfume | 0.01 |
| (14) | Titanium oxide | 1.0 |
| (15) | Purified water | Balance |

(Production Process)

After the ingredient (4) had been dissolved in the purified water (15), the ingredients (1), (2), (3), (6), (7), (8), and (9) were dissolved in the resulting solution. The ingredient (5) having been previously dissolved with heating in a part of the purified water was mixed with the aforesaid solution. Thereafter, the ingredients (11), (12), and (13) were mixed and dissolved in the ingredient (10), the ingredient (14) was dispersed in the resulting solution, and the external preparation was obtained by filtration.

Formulation Example 2

| (1) | Tartaric acid | 7.0 mass % |
|---|---|---|
| (2) | Glycerol | 7.0 |
| (3) | 1,3-Butylene glycol | 3.0 |
| (4) | Crosslinked type N,N-dimethylacrylamide-2-acrylamido-2-methylpropane sulfonic acid sodium salt copolymer | 2.0 |
| (5) | PEG-240/decyltetradeceth-20/HDI copolymer | 2.0 |
| (6) | L-Arginine | 0.5 |
| (7) | Sodium citrate | 1.0 |
| (8) | Sodium hydroxide | 0.5 |
| (9) | EDTA-2Na | 0.02 |

| | | |
|---|---|---|
| (10) | Ethanol | 5.0 |
| (11) | Tocopherol acetate | 0.01 |
| (12) | PEG-60 hydrogenated castor oil | 0.5 |
| (13) | Phenoxy ethanol | 0.3 |
| (14) | Perfume | 0.01 |
| (15) | Titanium oxide | 2.0 |
| (16) | Purified water | Balance |

(Production Process)

After the ingredient (4) had been dissolved in the purified water (16), the ingredients (1), (2), (3), (6), (7), (8), and (9) were dissolved in the resulting solution. The ingredient (5) having been previously dissolved with heating in a part of the purified water was mixed with the aforesaid solution. Thereafter, the ingredients (11), (12), (13), and (14) were mixed and dissolved in the ingredient (10), the ingredient (15) was dispersed in the resulting solution, and the external preparation was obtained by filtration.

With each of the external preparations for skin for use in the chemical peeling in accordance with the present invention, which preparations had been prepared in the Formulation Examples 1 and 2, the ease of pickup on a finger and the ease of washing away were excellent.

The invention claimed is:

1. An external preparation for skin, comprising ingredients (a), (b), and (c), wherein the external preparation for skin has a pH value within the range of 2.0 to 5.0 and is adapted to be removed after being applied to the skin:
    (a) at least one of the members selected from the group consisting of α-hydroxy acids, the ingredient (a) being contained in a containing quantity within the range of 1.0 to 7.0 mass %,
    (b) a crosslinked type N,N-dimethylacrylamide-2-acrylamido-2-methylpropane sulfonic acid sodium salt copolymer, the ingredient (b) being contained in a containing quantity within the range of 0.1 to 3.0 mass %, and
    (c) an associating thickener constituted of a compound that is represented by the following general formula (1), the ingredient (c) being contained in a containing quantity within the range of 0.1 to 3.0 mass %:

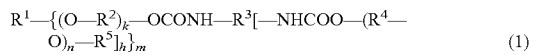

$$R^1-\{(O-R^2)_k-OCONH-R^3[-NHCOO-(R^4-O)_n-R^5]_h\}_m \quad (1)$$

wherein $R^1$ represents a hydrocarbon group, $R^2$ and $R^4$ independently represent alkylene groups having 2 to 4 carbon atoms, which alkylene groups may be identical or different from each other, or a phenylethylene group, $R^3$ represents a hydrocarbon group, which may optionally have a urethane bond, $R^5$ represents a branched chain or secondary hydrocarbon group, m represents a number of at least 2, h represents a number of at least 1, k represents a number within the range of 1 to 500, and n represents a number within the range of 1 to 200.

2. An external preparation for skin as defined in claim 1 wherein the associating thickener is a polyethylene glycol-240/decyltetradeceth-20/hexamethylene diisocyanate copolymer.

3. An external preparation for skin as defined in claim 1 wherein the containing ratio of the crosslinked type N,N-dimethylacrylamide-2-acrylamido-2-methylpropane sulfonic acid sodium salt copolymer, which is contained as the ingredient (b), to the associating thickener, which is contained as the ingredient (c), is selected within the range of (b):(c) of between 1:0.6 and 1:1.5.

4. An external preparation for skin as defined in claim 1 wherein the α-hydroxy acid is glycolic acid.

5. An external preparation for skin as defined in claim 1 wherein the external preparation for skin has a viscosity selected within the range of 10,000 to 30,000 mPa·s/30° C.

6. An external preparation for skin as defined in claim 1 wherein the external preparation for skin further contains titanium oxide as an ingredient (d).

7. An external preparation for skin as defined in claim 6 wherein the containing quantity of the titanium oxide contained as the ingredient (d) is selected within the range of 0.1 to 3 mass %.

8. An external preparation for skin as defined in claim 1 wherein the external preparation for skin is adapted for use in chemical peeling.

9. A cosmetics kit, comprising an external preparation for skin as defined in claim 1, a mask for use after the use of the external preparation for skin, and a night cream for use after the use of the mask.

10. An external preparation for skin as defined in claim 2 wherein the containing ratio of the crosslinked type N,N-dimethylacrylamide-2-acrylamido-2-methylpropane sulfonic acid sodium salt copolymer, which is contained as the ingredient (b), to the associating thickener, which is contained as the ingredient (c), is selected within the range of (b):(c) of between 1:0.6 and 1:1.5.

11. An external preparation for skin as defined in claim 2 wherein the α-hydroxy acid is glycolic acid.

12. An external preparation for skin as defined in claim 2 wherein the external preparation for skin further contains titanium oxide as an ingredient (d).

13. An external preparation for skin as defined in claim 11 wherein the external preparation for skin further contains titanium oxide as an ingredient (d).

14. An external preparation for skin as defined in claim 12 wherein the external preparation for skin is adapted for use in chemical peeling.

15. An external preparation for skin as defined in claim 11 wherein the external preparation for skin is adapted for use in chemical peeling.

16. A cosmetics kit, comprising an external preparation for skin as defined in claim 2, a mask for use after the use of the external preparation for skin, and a night cream for use after the use of the mask.

17. A cosmetics kit, comprising an external preparation for skin as defined in claim 11, a mask for use after the use of the external preparation for skin, and a night cream for use after the use of the mask.

* * * * *